United States Patent [19]

Tanaka

[11] 4,397,839

[45] Aug. 9, 1983

[54] SURFACE ACTIVE MATERIAL AND PROCESS FOR PREPARING SAME

[75] Inventor: Yuji Tanaka, Toda, Japan

[73] Assignee: Tokyo Tanabe Company, Limited, Japan

[21] Appl. No.: 354,628

[22] Filed: Mar. 4, 1982

[30] Foreign Application Priority Data

Sep. 10, 1981 [JP] Japan ................................ 56-141672

[51] Int. Cl.³ .............................................. A61K 35/12
[52] U.S. Cl. ....................................... 424/95; 424/199
[58] Field of Search .................................. 424/95, 199

[56] References Cited

PUBLICATIONS

Harwood et al.–Biochem. J., vol. 151, (1975), pp. 707–714.

King et al.–Am. J. Physiol., vol. 223, (Sep. 1972), pp. 707–726.

*Primary Examiner*—Sam Rosen
*Attorney, Agent, or Firm*—McGlew & Tuttle

[57] ABSTRACT

A surface active material having the capacity of reducing the surface tension in pulmonary alveoli significantly is provided. This material comprises, based on the dry weight of the material, 68.6–90.7% of phospholipid, 0.3–13.0% of neutral fat, 0.0–8.0% of total cholesterol, 1.0–27.7% of free fatty acids, 0.1–2.0% of carbohydrate, and 0.0–3.5% of protein. The material is produced by subjecting mammalian lung tissue to a series of procedures including acetic acid ester treatment, organic solvent mixture treatment, differential centrifugation, density gradient centrifugation and dialysis, and optionally adding a phosphatidylcholine, a neutral fat, and/or a free fatty acid to the resulting product. A pharmaceutical composition comprising the surface active material is usable for the clinical treatment of respiratory distress syndrome.

31 Claims, 6 Drawing Figures

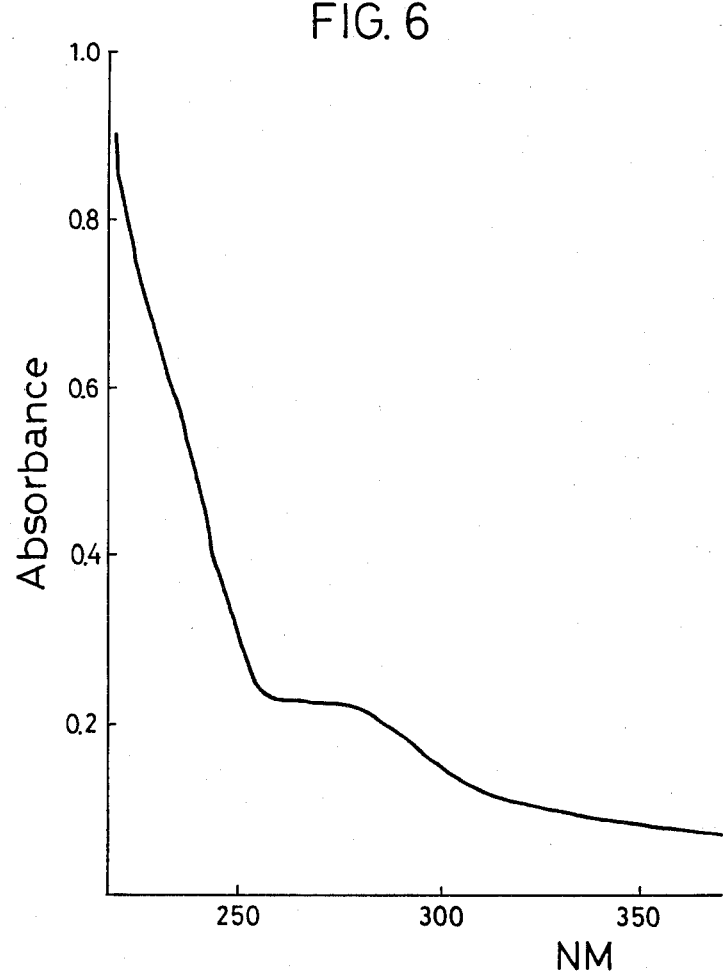

SURFACE ACTIVE MATERIAL AND PROCESS FOR PREPARING SAME

FIELD AND BACKGROUND OF THE INVENTION

This invention relates to a surface active material having a new chemical composition, a method of producing the same, and a pharmaceutical composition useable for the treatment of respiratory distress syndrome comprising the surface active material as active ingredient.

Respiratory distress syndrome (hereinafter referred to as RDS) is a highly fatal disease which frequently occurs in premature infants born after approximately 28–36 weeks of gestation and in adult patients with septicemia, uremia, postoperative shock, or toxicosis due to inhalation of poisonous chemicals and the like. It has been demonstrated that the main cause of RDS is atelectasis caused by a deficiency of the so-called pulmonary surfactant (i.e., the material that reduces intra-alveaolar surface tension quickly and lastingly and thereby makes respiratory movement smooth) and the deficiency arises from immature lung function or basic diseases.

As a substitute for such deficient pulmonary surfactant, a surface active material (hereinafter referred to as TA-546) comprising, in specific proportions, phospholipid, neutral fat, total cholesterol, carbohydrate and protein which are all obtained from the lung tissue of mammals has been disclosed in U.S. patent application Ser. No. 152048, filed May 21, 1980, now U.S. Pat. No. 4,338,301.

SUMMARY OF THE INVENTION

The present inventor has continued confirmatory studies on TA-546 and has found that it further contains less than 1.0% of free fatty acids in addition to the above-described components. This finding has led to the discovery that several important properties (i.e., surface tension-reducing capacity, spreadability over a liquid surface, and adsorbability to a gas-liquid interface) of TA-546 can be enhanced by increasing the relative amount or content of free fatty acids to 1.0–27.7% based on the total weight of TA-546.

The present invention is concerned with the improvement of TA-546 on the basis of the above-described discovery, as well as the provision of a pharmaceutical composition useable in the treatment of RDS in adults and premature infants.

According to one feature of the present invention, there is provided a surface active material comprising (1) phospholipid, neutral fat, total cholesterol, free fatty acids, carbohydrate, protein and water, all of which are obtained from the lung tissue of a mammal, and (2) optionally at least one additional component selected from the group consisting of a phosphatidylcholine, a neutral fat and a free fatty acid, characterized in that the overall phospholipid content is 68.6–90.7%, the overall neutral fat content is 0.3–13.0%, the total cholesterol content is 0.0–8.0%, the overall free fatty acid content is 1.0–27.7%, the carbohydrate content is 0.1–2.0%, the protein content is 0.0–3.5%, and the water content is 2.1–5.2%, all based on the dry weight of the material, the surface tension of the material as measured at 15°–25° C. by Wilhelmy's method in which the material is added dropwise to the surface of physiological saline in an amount of 0.3–0.8 μg per square centimeter of the surface area thereof being 30.1–47.5 dynes/cm when the surface area is 54.0 cm$^2$.

According to another feature of the present invention, there is provided a method of producing a surface active material as set forth above, which comprises the steps of (a) bringing the minced lung tissue of a mammal into contact with an electrolyte solution to obtain an extract; (b) centrifuging the extract to collect a crude sediment; (c) adjusting the specific gravity of an aqueous suspension of the crude sediment by the addition of sodium chloride and centrifuging the adjusted suspension to isolate a top layer comprising an emulsified scum layer; (d) dialyzing an aqueous suspension of the top layer and lyophilizing the dialyzed suspension to obtain a crude dry product; (e) bringing the crude dry product into contact with an acetic acid ester to collect a material insoluble in the acetic acid ester and then bringing the insoluble material into contact with an organic solvent mixture to obtain a purified filtrate; and (f) concentrating the purified filtrate to obtain a solid residue, optionally adding to the solid residue at least one additional component selected from the group consisting of phosphatidylcholines, neutral fats and free fatty acids, so as to provide an overall phospholipid content of 68.6–90.7%, an overall neutral fat content of 0.3–13.0%, and an overall free fatty acid content of 1.0–27.7%, all based on the dry weight of the final product, as well as an overall phosphatidylcholine content of 58.4–85.0% based on the total weight of phospholipid, and then lyophilizing the resulting mixture.

According to still another feature of the present invention, there is provided a pharmaceutical composition useable for the treatment of RDS comprising an effective amount of a surface active material as set forth above and a pharmaceutically acceptable carrier thereof.

For an understanding of the principles of the invention, reference is made to the following description of typical embodiments thereof as illustrated in the accompanying drawings.

BRIEF DESCRIPTION OF THE DRAWINGS

In the drawings:

FIG. 6 is an ultraviolet absorption spectrum of the surface active material of the invention.

DESCRIPTION OF THE PREFERRED EMBODIMENTS

Figure 1:
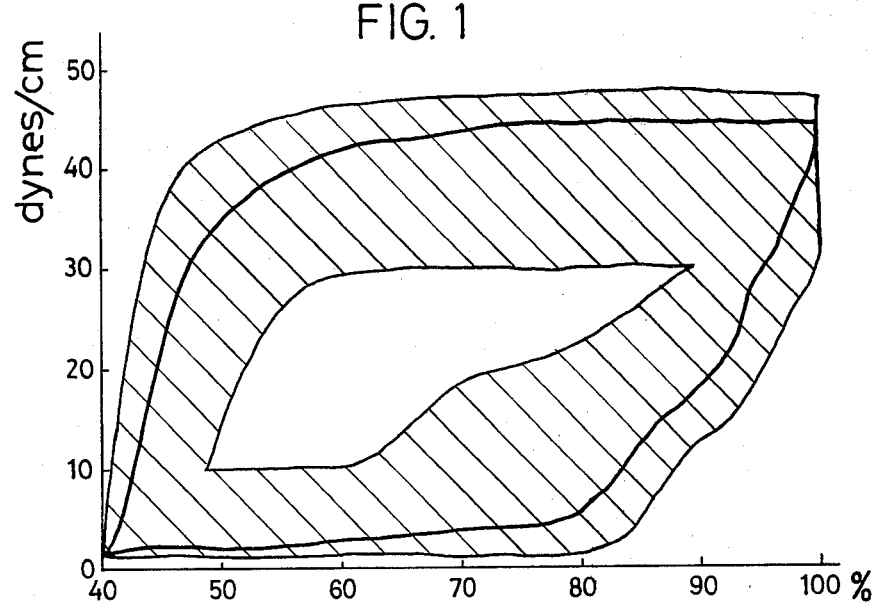
FIGS. 1 to 4 are diagrammatic illustrations of hysteresis curves showing the surface tension of physiological saline against the surface area thereof.
Figure 2:
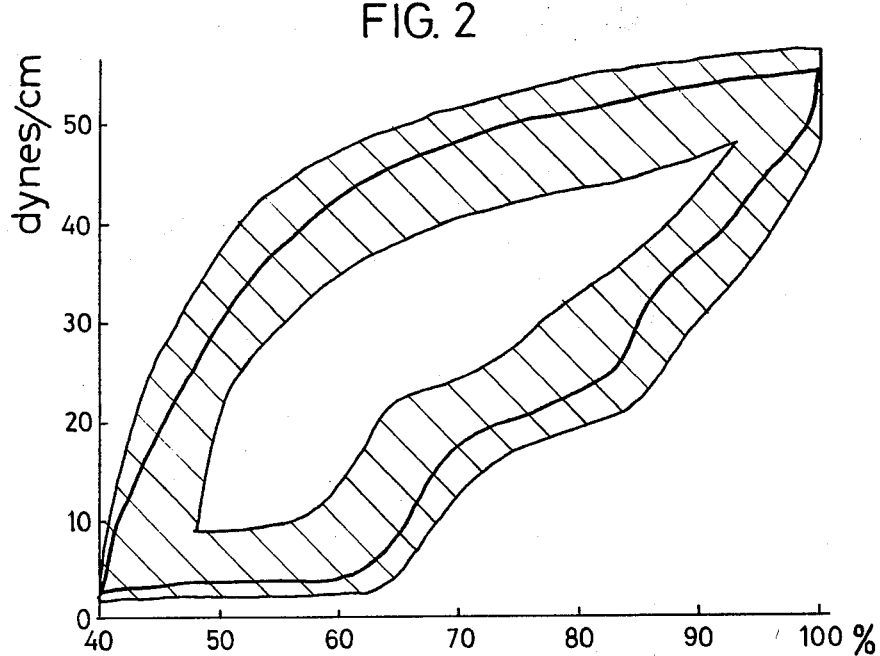
Figure 3:
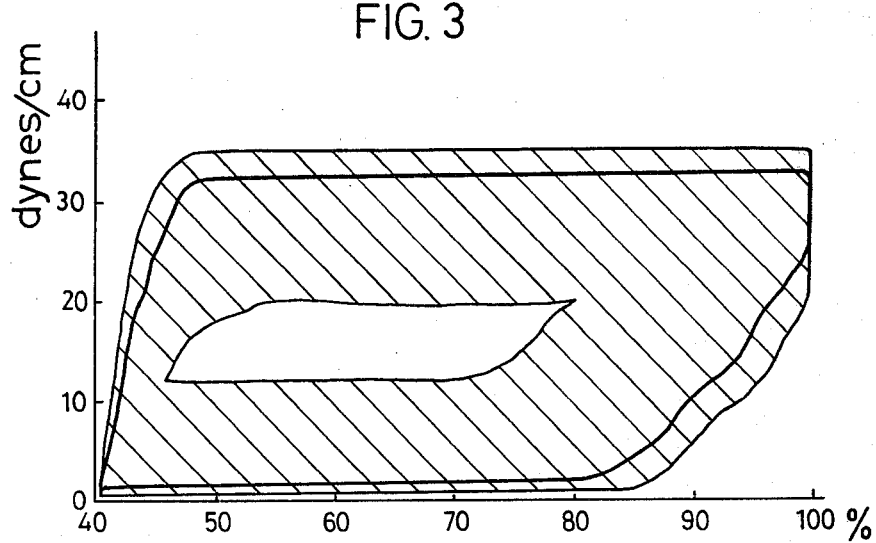
Figure 4:
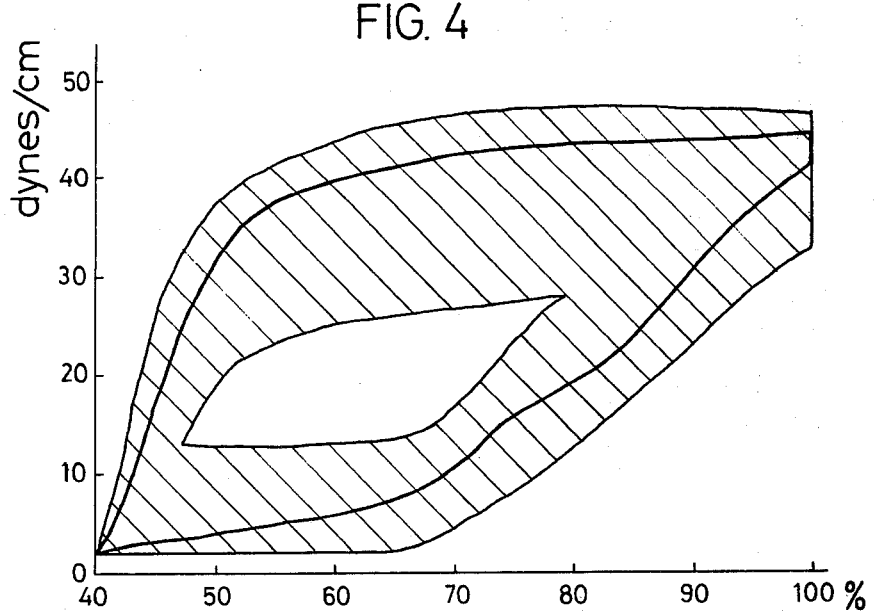

FIGS. 1 to 4 diagrammatically illustrate hysteresis curves recorded by measuring the surface tension of physiological saline with an Acoma Wilhelmy surface tension balance (Acoma Igaku Kogyo Co., Ltd.) and plotting the measured data with an X-Y recorder (Model F-3D; Riken Denshi Co., Ltd.). In each figure, the shaded portion indicates the region into which the recorded hysteresis curves fall, and the bold solid line represents an exemplary hysteresis curve. In FIGS. 1 and 2, measurements were made at 15°–25° C. after the surface active material of the invention and TA-546, respectively, were added dropwise to the surface of physiological saline in an amount of 0.3–0.8 μg per square centimeter of the surface area. In FIGS. 3 and 4, measurements were made at 37° C. after the material of the invention and TA-546, respectively, were added dropwise to the surface of physiological saline in an amount of 1.0–2.0 μg per square centimeter of the surface area. In these figures, the surface tension is plotted as ordinate and the surface area expressed in percentage of the maximum surface area (54.0 cm$^2$) as abscissa.

Figure 5:
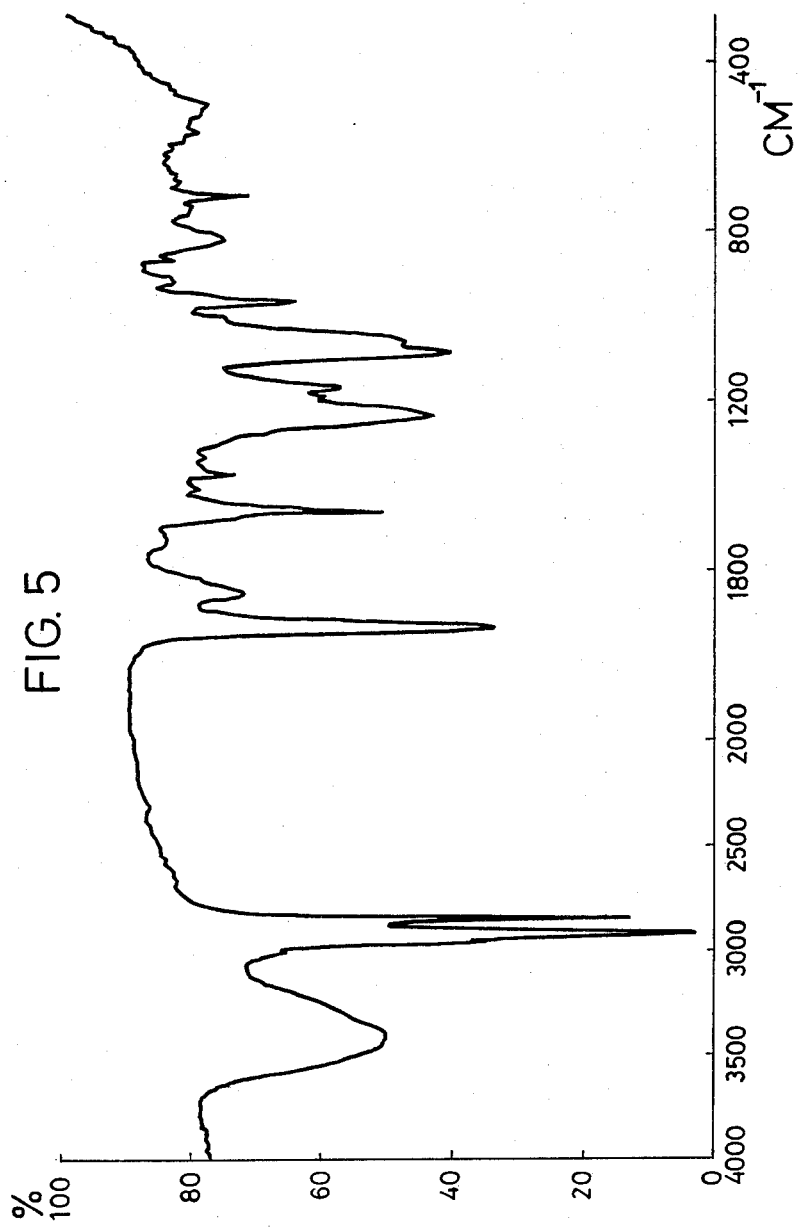
FIG. 5 is an infrared absorption spectrum of the surface active material of the invention.

FIG. 5 is an infrared absorption spectrum of the material of the invention as measured in a KBr tablet.

FIG. 6 is an ultraviolet absorption spectrum of the material of the invention as measured in a 0.1% (w/v) solution in cyclohexane-ethanol (with a volume ratio of 1:1).

The chemical composition, physicochemical properties and pharmacological properties of the surface active material provided by the present invention are described in detail below. For purposes of comparison, the data on TA-546 are also given which have been disclosed in the aforementioned U.S. patent application or were obtained in the above-described confirmatory studies.

[I] Chemical Composition

The surface active material of the invention comprises those specific components (i.e., phospholipid, neutral fat, total cholesterol, free fatty acids, carbohydrate and protein) which are obtained from the lung tissue of mammals such as cattle, horses, sheep, and pigs. Table I shows the contents (in percent by weight) of the above-enumerated components (including acylglycerols constituting the neutral fat as well as free and esterified cholesterols constituting the total cholesterol) based on the total dry weight of the material, the contents (in percent by weight) of phospholipid constituents based on the total weight of phospholipid, and the content (in percent by weight) of phosphatidylcholine having two saturated fatty acid residues based on the total weight of phosphatidylcholine.

The phospholipid content was estimated by measuring its phosphorus content according to a procedure based on the method of King et al. (Biochemical Journal, 26, 292, 1932) and then multiplying the measured value by 25. The carbohydrate content was measured according to a procedure based on the phenol-sulfuric acid method (Analytical Chemistry, 28, 350, 1956) and expressed in terms of glucose. The protein content was measured according to a procedure based on the method of Lowry et al. (Journal of Biological Chemistry, 193, 265, 1956) and expressed in terms of bovine serum albumin. The water content was measured according to Karl Fischer's method.

The chemical composition of the phospholipid comprised in the material was analyzed as follows: The constitutes of the phospholipid were separated by two-dimensional thin-layer chromatography using a 20 cm×20 cm thin layer of silica gel 60 (0.25 mm in thickness; manufactured by Merck Co.). Then, each fraction was taken and estimated by a modification of the above-described procedure for the measurement of phospholipid content. Two-dimensional development was carried out with chloroform-methyl alcohol-water (in the volume ratio of 65:25:4) as the first solvent and chloroform-methyl alcohol-7 N aqueous ammonia (in the volume ratio of 230:90:15), and the spots were made visible with iodine.

The content of phosphatidylcholine having two saturated fatty acid residues was measured as follows: Using the method of shimojo et al. (Journal of Lipid Research, 15, 525, 1974), the constituents of the phosphatidylcholine comprised in the material were separated according to the type of fatty acid residues. Then, the fraction containing phosphatidylcholine having two saturated fatty acid residues was taken and estimated by a modification of the above-described procedure for the measurement of phospholipid content.

In estimating the neutral fat, total cholesterol and free fatty acid contents, the surface active material of the invention was fractionated by thin-layer cromatography using a thin layer of Silica Gel 60 (0.25 mm in thickness, 5×20 cm in size; Merck Co.). Then, the fractions corresponding to each component were isolated and subjected to quantitative analysis. A mixture of petroleum ether and ether (in a volume ratio of 3:1) was used as the developing solvent, and iodine as the color developer. The neutral fat content was estimated by determining the fractionated mono-, di- and triacylglycerols according to the acetylscetone colorimetric method (Clinica Chimica Acta, 22, 393, 1968), expressing them in terms of mono-, di- and trioleoylglycerols, and then calculating the sum total thereof. The total cholesterol content was estimated by determining the fractionated free cholesterol and cholesterol esters according to the o-phthalaldehyde method (Analytical Biochemistry, 29, 143, 1969), expressing them in terms of free cholesterol and chlesterol palmitate, and then calculating the sum total thereof. The free fatty acid content was estimated by determining the fractionated free fatty acids according to the method of Itaya et al. (Journal of Lipid Research, 6, 16, 1965) and expressing them in terms of palmitic acid.

TABLE I

| | Surface active material of the invention | TA-546 |
|---|---|---|
| Composition of surface active material | | |
| Phospholipid | 68.6–90.7% | 75.0–95.5% |
| Neutral fat | 0.3–13.0% | 1.8–14.0% |
| ⌈ Triacylglycerols | 0.2–10.0% ⌉ | |
|   Diacylglycerols | 0.1–2.5% | |
| ⌊ Monoacylglycerols | 0.0–0.5% ⌋ | |
| Total cholesterol | 0.0–8.0% | 0.0–3.0% |
| ⌈ Free cholesterol | 0.0–6.5% ⌉ | |
| ⌊ Cholesterol esters | 0.0–1.5% ⌋ | |
| Free fatty acids | 1.0–27.7% | (Less than 1.0%) |
| Carbohydrate | 0.1–2.0% | 0.1–1.5% |
| Protein | 0.0–3.5% | 0.5–5.0% |
| Water | 2.1–5.2% | 1.7–6.0% |
| Phospholipid constituents | | |
| Phosphatidylcholine | 58.4–85.0% | 63.0–85.5% |
| Phosphatidylglycerol | 0.1–12.0% | 3.0–12.0% |
| Phosphatidylethanolamine | 3.5–12.6% | 2.5–7.7% |
| Sphingomyelin | 3.2–12.1% | 5.7–7.0% |
| Phophatidylinositol | 1.2–6.6% | |
| | | 2.4–7.4% |
| Phosphatidylserine | 1.0–6.4% | |
| Lysophosphatidycholine | 0.1–2.9% | 0.5–2.1% |
| Others | 0.0–5.0% | 1.0% or less |
| Content of phosphatidylcholine having two saturated fatty acid residues | 61.3–87.5% | 67.5–90.3% |

[II] Physicochemical Properties
(i) Surface tension-reducing capacity

The surface active material of the invention was added dropwise to the surface of physiological saline having a surface area of 54.0 cm², in an amount of 0.3–0.8 µg/cm² at a temperature of 15°–25° C. or 1.0–2.0 µg/cm² at a temperature of 37° C. Then, according to Wilhelmy's method, the surface tension of the physiological saline was continuously measured while its surface area was being decreased and then increased between 54.0 cm² and 21.6 cm² over a period of 2–5 minutes (FIGS. 1 and 3). The results thus obtained are shown in Table II. The surface tension of physiological saline alone was 72.0 dynes/cm at 15°–25° C. and 70.5 dynes/cm at 37° C.

TABLE II

|  | Surface active material of the invention | TA-546 |
|---|---|---|
| Highest surface tension (dynes/cm) |  |  |
| at 15–25° C. | 30.1–47.5 | 48.2–58.0 |
| at 37° C. | 21.0–35.6 | 32.3–47.5 |
| Lowest surface tension (dynes/cm) |  |  |
| at 15–25° C. | 1.5–10.3 | 2.1–8.6 |
| at 37° C. | 1.8–12.0 | 2.0–12.2 |

It can be seen from Table II that the material of the invention reduced the maximum surface tension of physiological saline by factors of 48.0 at a maximum and 1.5 at a minimum when measurements were made at 15°–25° C., and by factors of 39.2 at a maximum and 1.9 at a minimum when measurements were made at 37° C.

(ii) Spreadability over a liquid surface

The surface active material of the invention was added dropwise to the surface of physiological saline kept at 37° C., in an amount of 0.8–1.5 µg/cm² of surface area. As soon as the material was added, the change of its surface tension with time was measured according to the vertical plate method. The surface tension of physiological saline decreased from an initial value of 70.5 dynes/cm and, after 10 seconds, reached a constant value in the range of 18.0–35.1 dynes/cm. This indicates that, within only 10 seconds after addition of the material of the invention, a monomolecular film having great capacity for reducing surface tension was formed in the gas-liquid interface. In other words, the material of the invention spread very rapidly over the liquid surface. When the surface tension of physiological saline was measured in the same manner except that the material of the invention was replaced by TA-546, the time required for the surface tension to reach a constant value was as long as 120 seconds and the constant value was as high as 26.3–48.1 dynes/cm.

(iii) Adsorbability to a gas-liquid interface

A suspension containing 20–100 µg of the surface active material of the invention per ml of physiological saline and having no floating matter was prepared at 37° C. Thus, the adsorption rate of the suspended material to the gas-liquid interface was estimated according to the method of King et al. (American Journal of Physiology, 223, 715, 1972). Specifically, as soon as the suspension was prepared, the change of its surface tension with time was measured. The surface tension decreased from an initial value of 70.5 dynes/cm and, after 30 seconds, reached a constant value in the range of 16.8–39.9 dynes/cm. This indicates that, within 30 seconds after being suspended, the material of the invention rose and became adsorbed to the gas-liquid interface and formed a monomolecular film having strong surface activity. When the surface tension of a suspension was measured in the same manner except that the material of the invention was replaced by TA-546, the time required for the surface tension to reach a constant value was as long as 150 seconds and the constant value was as high as 33.2–55.0 dynes/cm.

(iv) Optical activity

When measured with an automatic polarimeter (Model DIP-180; Nihon Bunko Co., Ltd.), the specific rotatory power $[\alpha]_D^{26}$ of the material of the invention was found to be +2.0 to +7.2 (C=0.2 in benzene).

(v) Solubility

Aqueous suspensions of the material of the invention were found to be weakly acidic. The solubility of the material of the invention in various solvents is shown in Table III. Specifically, 10 mg of the material was added to 10 ml of each solvent and the resulting mixture was stirred for approximately 10 seconds. The solubility was expressed as positive (+) when the material dissolved visually, or as negative (−) when the material did not dissolve visually.

TABLE III

| Solvent | Volume ratio | Solubility |
|---|---|---|
| Chloroform |  | + |
| Benzene |  | + |
| Water |  | − |
| Methanol |  | − |
| Ethanol |  | − |
| Acetone |  | − |
| Ethyl acetate |  | − |
| Cyclohexane-ethanol | 1:1 | + |
| Ethyl ether-ethanol | 1:1 | + |
| Petroleum ether-ethanol | 1:1 | + |
| Acetone-methanol | 1:1 | − |
| Chloroform-methanol | 2:1 | + |

(vi) Absorption spectra

Infrared and ultraviolet absorption spectra of the material of the invention are illustrated in FIGS. 2 and 3, respectively.

[III] Pharmacological Properties (i) Acute toxicity

The acute toxicity of the surface active material of the invention was tested by administering it orally or intraperitoneally to 5-weeks-old male ICR mice and Wistar rats. For mice, the oral and intraperitoneal $LD_{50}$ values were not less than 3.0 g/kg and not less than 2.0 g/kg, respectively. For rats, the oral and intraperitoneal $LD_{50}$ values were not less than 4.0 g/kg and not less than 2.5 g/kg, respectively.

(ii) Subacute toxicity

The surface active material of the invention was administered intraperitoneally to mature Wistar rats in a daily dose of 0.5 g/kg of body weight for a period of one month. No significant change in body weight was noted. Moreover, visual observation and histological examination revealed no abnormalities.

(iii) Intra-alveaolar surface tension-reducing capacity (a) Alveolar volume-maintaining effect Using 7 rabbit fetuses removed after 27 days of gestation, the alveolar volume change at decreasing endotracheal pressures (hereinafter referred to as the PV curve) was measured. Specifically, the neck of each fetus was incised to expose the trachea, to which a water monometer was connected directly. Beginning at 5 minutes after treatment with the surface active material of the invention, the alveolar volume was measured continuously. The endotracheal pressures was varied by means of an independently-acting 2-channel syringe pump (No. 940; Harvard Inc.) connected to the trachea. The treatment with the material of the invention was carried out by preparing a 1.0-1.5% (w/v) suspension of the material in physiological saline and instilling 0.4-0.5 ml of the suspension directly into the trachea. These measuring conditions were substantially the same as those described in the aforementioned U.S. patent application. In a control group, measurements were made in the same manner except that the suspension of the material of the invention was replaced by physiological saline. The alveolar volume was expressed as the number of milliliters per kilogram of body weight. The results thus obtained are shown in Table IV.

TABLE IV

| Endotracheal pressure (cmH$_2$O) | Alveolar volume (ml/kg) | | |
|---|---|---|---|
| | Control group | Group treated with the surface active material of the invention | Group treated with TA-546 |
| 35 | 14 ± 5 | 72 ± 10 | 55 ± 2 |
| 25 | 12 ± 5 | 71 ± 11 | 49 ± 3 |
| 20 | 11 ± 4 | 70 ± 9 | 47 ± 3 |
| 15 | 10 ± 4 | 66 ± 9 | 44 ± 3 |
| 10 | 6 ± 3 | 58 ± 8 | 39 ± 4 |
| 5 | 2 ± 2 | 46 ± 10 | 25 ± 3 |
| 0 | 0 | 24 ± 9 | 17 ± 4 |

(b) Intra-alveolar pressure-reducing effect

Using 5 rabbit fetuses removed after 27 days of gestation and placed under artificial respiration, the endotracheal pressure required to maintain the ventilation volume per respiration at 10 ml/kg of body weight was measured with a respirometer (MFP-1100; Nihon Koden Co., Ltd.). This measurement was made 5 minutes after instilling into the airway 0.4 ml of a 1.0% (w/v) suspension of the surface active material of the invention in physiological saline. The value of endotracheal pressure obtained with the material of the invention was 8 cmH$_2$O, while that obtained with TA-546 was 12 cmH$_2$O.

(iv) Respiratory function-improving capacity (a) Effects on RDS arising from septicemia The respiratory function-improving capacity of the surface active material of the invention was tested on mature rabbits suffering from septicemia which had been induced by intraperitoneal inoculation of *Escherichia coli* and further complicated by RDS. Specifically, 32 rabbits in the abovedescribed morbid state were divided into 4 groups including one control (or no-treatment) group. The other groups were treated with kanamycin sulfate alone, the material of the invention alone, and a combination of kanamycin sulfate and the material of the invention, respectively. Then, all groups were comparatively examined for the degree of improvement in respiratory function. The morbid rabbits were prepared and the degree of lung injury was evaluated according to the methods of Cuevas et al. (Archives of Surgery, 104, 319, 1972), and the circulating titer of endotoxin in blood was determined according to the method of Reinhold et al. (Proceedings of the Society for Experimental Biology and Medicine, 137, 334, 1971). The treatment with the material of the invention and/or kanamycin sulfate was carried out within 24 hours before and after the onset of RDS. The material of the invention was instilled 1-6 times into the airway in a dose of 50-100 mg/kg for each treatment, while 80-150 mg/kg of kanamycin sulfate was intramuscularly injected in 2-8 divided doses. Two days after treatment, the subjects were examined for survival and the degree of lung injury. The results thus obtained are shown in Table V. With regard to the animals that had died, the degree of lung injury observed immediately before their was employed. The degree of lung injury becomes severer as the value increases.

TABLE V

| Group | Subject No. | Circulating titer (μg/ml) | Degree of lung injury | Survival |
|---|---|---|---|---|
| Control group | 1 | 3.00 | 3 | No |
| | 2 | 0.10 | 3 | No |
| | 3 | 0.20 | 2 | No |
| | 4 | 0.10 | 3 | No |
| | 5 | 1.00 | 1 | No |
| | 6 | 1.00 | 3 | No |
| | 7 | 0.40 | 3 | No |
| | 8 | 0.40 | 2 | No |
| Group treated with kanamycin sulfate alone | 9 | 0.10 | 3 | No |
| | 10 | 0.01 | 0 | Yes |
| | 11 | 0.00 | 1 | Yes |
| | 12 | 0.40 | 2 | No |
| | 13 | 0.10 | 2 | No |
| | 14 | 0.10 | 1 | No |
| | 15 | 0.02 | 0 | Yes |
| | 16 | 0.10 | 1 | Yes |
| Group treated with the material of the invention alone | 17 | 0.02 | 0 | Yes |
| | 18 | 0.10 | 3 | No |
| | 19 | 0.01 | 0 | Yes |
| | 20 | 0.50 | 1 | No |
| | 21 | 0.40 | 2 | No |
| | 22 | 0.10 | 0 | Yes |
| | 23 | 0.02 | 0 | Yes |
| | 24 | 0.20 | 1 | No |
| Group treated with kanamycin sulfate and the material of the invention | 25 | 0.01 | 1 | Yes |
| | 26 | 0.02 | 2 | Yes |
| | 27 | 0.05 | 0 | Yes |
| | 28 | 0.00 | 0 | Yes |
| | 29 | 0.10 | 2 | No |
| | 30 | 0.01 | 1 | Yes |
| | 31 | 0.05 | 0 | Yes |
| | 32 | 0.01 | 1 | Yes |

It is evident from Table V that, when used alone, the material of the invention brought about a greater improvement in respiratory function than might have been expected. Moreover, the combined use of the material of the invention and kanamycin sulfate almost completely restored the respiratory function to normal.

(b) Effects on a model for RDS in adult patients

The respiratory function-improving power of the surface active material of the invention was tested on guinea pigs suffering from RDS experimentally induced by lavage of the lungs. Specifically, 16 guinea pigs in the above-described morbid state were divided into two groups. In one group, the animals were placed under respiratory management and allowed to stand for 6 hours. In the other group, the surface active material of the invention was administered to the animals 3 hours after the commencement of respiratory management. Thereafter, the animals were allowed to stand for an additional 3 hours. The animals of both groups were killed by exsanguination and used to measure their PV curves, which were compared with the PV curve measured separately with normal guinea pigs. The morbid guinea pigs were prepared and the respiratory management was done according to the methods of Lachmann et al. (Acta Anaesthesiologica Scandinavica, 24, 231, 1980), and the PV curves were measured in substantially the same manner as described above. The treatment with the material of the invention was carried out by preparing a 1.0% (w/v) suspension of the material in physiological saline and instilling the suspension into the airway in a dose of 60 mg/kg. The results thus obtained are shown in Table VI.

TABLE VI

| Endotracheal pressure (cmH$_2$O) | Alveolar volume (ml/kg) | | |
|---|---|---|---|
| | Control group | Group treated with the surface active material of the invention | Normal group |
| 30 | 7.2 ± 3.3 | 17.2 ± 2.7 | 17.5 ± 3.1 |
| 25 | 6.8 ± 2.8 | 16.4 ± 2.5 | 16.3 ± 2.8 |
| 20 | 5.2 ± 2.1 | 15.8 ± 2.4 | 16.0 ± 2.7 |
| 15 | 4.6 ± 1.7 | 14.2 ± 2.2 | 14.4 ± 2.5 |
| 10 | 3.8 ± 1.6 | 13.8 ± 2.0 | 13.6 ± 2.0 |
| 5 | 1.5 ± 0.9 | 10.6 ± 1.8 | 10.2 ± 1.6 |
| 0 | 0 | 5.4 ± 1.2 | 5.2 ± 1.6 |

It is evident from Table VI that the material of the invention almost completely restored the respiratory function to normal.

Judging from the chemical composition, physicochemical properties and pharmacological properties described in detail above, pharmaceutical compositions comprising the surface active material of the invention can be regarded as markedly effective and quick-acting remedies for RDS.

In the treatment of RDS, the pharmaceutical composition of the invention is used in such a dose as to provide 50-400 mg or 500-3,000 mg of the surface active material of the invention for premature infants or adults, respectively. This dose is administered by suspending it in water or an electrolyte solution such as physiological saline so as to give a concentration of 1.0-5.0% (w/v), and then instilling or spraying the resulting suspension into the airway of the patient. For premature infants, the treatment should be carried out within 72 hours after their birth, while for adult patients, within 120 hours before or after the onset of respiratory distubance. The number of treatments preferably ranges from 1 to 10. The above-described dosage, method of administration, and number of treatments may be modified depending on the symptoms of the patient and the concomitantly used remedies. For adult patients, it is desirable to use the pharmaceutical composition of the invention in combination with a suitable remedy for the basic disease.

The pharmaceutical composition of the invention may contain suitable additives (e.g., stabilizers, preservatives, osmotic pressure regulators, buffering agents and/or suspending agents) and germicides as required. Preferably, the pharmaceutical composition of the invention is in the form of a liquid or a powder which is intended to be made into a suspension prior to use.

The pharmaceutical composition of the invention is charged into hermetically sealed containers such as vials and ampules, and thereby stored aseptically.

The method of producing the surface active material of the present invention is specifically described below with reference to a preferred embodiment thereof.

(a) Lungs which have been excised from a mammal are cut into fist-sized lumps, free of unnecessary blood vessels, windpipes, fat bodies, blood and the like, and then minced finely with a meat grinder. The resulting lung mince is brought into contact with an electrolyte solution such as physiological saline. This contact is effected, with stirring, at 0°-20° C. for 15-120 minutes. The mixture so prepared was filtered under pressure to obtain an extract. As the mammal, cattle, horses, sheep or pigs are suitably used. It is more advantageous to use their sucklings. If desired, the lung mince may be lyophilized and stored until it is subjected to the extraction procedure.

(b) The above extract is centrifuged at 8,000-20,000 r.p.m. at 0°-10° C. to collect a crude sediment. The unnecessary lung fragments remaining in this crude sediment are removed by re-suspending the crude sediment in an electrolyte solution such as physiological saline and centrifuging the resulting suspension at 500-2,000 r.p.m.

(c) The crude sediment obtained as above is suspended in water. To the resulting suspension is added sodium chloride or the like so as to adjust its specific gravity to 1.10-1.20. The adjusted suspension is centrifuged at 5,000-13,000 r.p.m. at 0°-10° C. for 20-180 minutes to divide it into three layers, the top layer being an emulsified scum layer. This top layer is isolated and purified by re-suspending it in a 12.5-26.0% (w/v) aqueous sodium chloride solution and centrifuging the resulting suspension at a medium speed. If necessary, this purification procedure may be repeated several times.

(d) The purified top layer is suspended in water and the resulting suspension is dialyzed at 4°-10° C. for 6-24 hours through a cellophane membrane against water. Thereafter, the dialyzed suspension is lyophilized to obtain a crude dry product. The dialysis is carried out for the purpose of removing the unnecessary inorganic salts and low-molecular water-soluble organic materials contained in the top layer. The purity of the crude dry product can be enhanced by resuspending the crude dry product in an electrolyte solution such as physiological saline, laying the resulting suspension on a 0.25-0.80 M sucrose solution, and centrifuging them at 22,000-50,000 r.p.m. at 0°-6° C. for 1-24 hours. However, this purification procedure is not essential to the method of the invention.

(e) The above crude dry product is suspended in a cold acetic acid ester at a temperature of −10° to 10° C., the amount of acetic ester used being equal to 20-300 times the weight of the crude dry product. The resulting suspension is allowed to stand for 30-60 minutes. Thereafter, a material insoluble in the acetic acid ester is separated and dried. Then, this insoluble material is brought into an organic solvent mixture, the amount of organic solvent mixture used being equal to 20-200 times the weight of the insoluble material. The resulting mixture is allowed to stand for 10-20 minutes and then filtered to obtain purified filtrate. The treatment with an acetic acid ester serves to remove the total cholesterol remaining in excess, and the treatment with an organic solvent mixture serves to remove any unnecessary protein. Useful acetic acid esters include methyl acetate, ethyl acetate, propyl acetate and butyl acetate, and useful organic solvent mixtures include chloroform-methanol (with a volume ratio of 2:1), chloroform-ethanol (with a volume ratio of 2:1), chloroform-isopropanol (with a volume ratio of 2:1) and ether-ethanol (with a volume ratio of 1:3). The sterility of the purified filtrated thus obtained is confined by testing it according to the procedure described in the Japanese Pharmacopoeia (9th edition), p. B-232. Thereafter, all subsequent operations are carried out under sterile conditions.

(f) The above purified is washed for 1-24 hours with sterile water and then concentrated under reduced pressure to obtain a solid residue. Where the chemical composition of this solid residue falls within the range defined hereinabove, the solid residue is directly lyophilized to obtain a final product which is within the scope of the invention. However, it commonly happens that, in the chemical composition of the solid residue, the phospholipid content is less than 68.6%, the neutral fat content is less than 0.3%, and/or the free fatty acid content is less than 1.0%. Moreover, it may happen that, even if the phospholipid content is not less than 68.6%, the content of phosphatidylcholine as the main constituent thereof is less than 58.4% based on the total weight of phospholipid. Furthermore, both may be the case. In such circumstances, at least one additional component selected from the group consisting of a phosphatidylcholine, a neutral fat and a free fatty acid is added so as to make up for the deficient component or components and thereby provide an overall phospholipid content of 68.6-90.7%, an overall neutral fat content of 0.3-13.0%, and an overall free fatty acid content of 1.0-27.7%, all based on the total dry weight of the final product, as well as an overall phosphatidylcholine content of 58.4-85.0% based on the total weight of phospholipid. Thereafter, the resulting mixture is lyophilized to obtain a final product. The phosphatidylcholines, neutral fats and free fatty acids which can be used as additional components include both synthetic materials and materials extracted from animals or plants. Preferably, the phosphatidylcholine used as an additional component is dipalmitoylphosphatidylcholine; the neutral fat used as an additional component is a member selected from the group consisting of tripalmitoylglycerol, tristearoylglycerol, trioleoylglycerol and mixtures thereof; and the free fatty acid used as an additional component is a member selected from the group consisting of palmitic acid, stearic acid, oleic acid and mixtures thereof.

Some examples of the pharmaceutical compositions prepared according to the present invention are given below.

PHARMACEUTICAL COMPOSITION 1

One thousand mg of the surface active material of the present invention was accurately weighed out and charged into a 30-ml vial under sterile conditions according to a conventional powder filling technique, followed by sealing the vial with a metal-clamped rubber stopper. This vial was accompanied with 25 ml of sterile physiological saline in order to prepare a suspension therewith prior to use.

PHARMACEUTICAL COMPOSITION 2

Sixty mg of the surface active material of the present invention was accurately weighed out and charged into a 10-ml ampule together with 6 ml of physiological saline. Then, the ampule was sealed under sterile conditions.

The present invention is further illustrated by the following examples. Unless otherwise indicated, percentages are by weight.

EXAMPLE 1

(a) Lungs (32.0 kg) excised from cattle were washed with water to remove any blood and other contaminants adhering thereto. Then, the lungs were cut into fist-sized lumps and freed of unnecessary blood vessels, windpipes and the like with the aid of scissors. These lumps were finely minced with a meat grinder to obtain 30 kg of lung mince. This lung mince was mixed with 120 liters of physiological saline. The resulting mixture was stirred under ice-cold conditions, placed in a filter bag, and filtered under pressure to obtain an extract. This procedure was repeated four times. The combined volume of the resulting extract was 130 liters.

(b) The above extract was centrifuged at 8,000 r.p.m. at 4° C. for 1 hour to collect a crude sediment. This crude sediment was suspended in 20 liters of physiological saline and then centrifuged at 2,000 r.p.m. for 10 minutes to precipitate off any residual tissue fragments and the like. The suspension obtained as the top layer was centrifuged again at 8,000 r.p.m. to collect a crude sediment. This purification procedure was repeated three times.

(c) The crude sediment obtained as above was suspended in 20 liters of water. To the resulting suspension was added 5.7 kg of sodium chloride so as to adjust its specific gravity to approximately 1.20. The adjusted suspension was centrifuged at 8,000 r.p.m. for 45 minutes to divide it into three layers, the top layer being an emulsified scum layer. This top layer was isolated and purified by re-suspending it in 10 liters of a 26.0% (w/v) aqueous sodium chloride solution and centrifuging the resulting suspension at 8,000 r.p.m. for 45 minutes.

(d) The purified top layer was suspended in distilled water and the resulting suspension was dialyzed through a cellophane membrane against distilled water. Thereafter, the dialyzed suspension was lyophilized to obtain 220 g of crude dry product.

(e) To this crude dry product was added 11 liters of cold ethyl acetate at 5° C. The resulting mixture was stirred for 30 minutes and then filtered under reduced pressure to separate an insoluble material. After this insoluble material was dried, 7 liters of an organic solvent mixture or chloroform-methanol (with a volume ratio of 2:1), was added thereto. The resulting mixture was stirred for 30 minutes and then filtered through filter paper to obtain a purified filtrate. To the filtration residue was added 7 liters of the same mixed solvent. The resulting mixture was stirred for 30 minutes and then filtered through filter paper to obtain a secondary purified filtrate. This procedure was repeated once more to obtain a tertiary purified filtrate. The combined volume of the purified filtrate thus obtained was 21 liters. When a sterility test was made on a small sample of this purified filtrate, it was found to be sterile. Accordingly, all subsequent operations were carried out under sterile conditions.

(f) The above purified filtrate was concentrated under reduced pressure to obtain 37.0 g of solid residue. When a small sample of this solid residue was lyophilized and then analyzed, the solid residue was found to have a phopholipid content of 78.5%, a neutral fat content of 10.3%, and a free fatty acid content of 0.5%, all based on the total dry weight thereof, as well as a phosphatidylcholine content of 50.8% based on the total weight of phospholipid. Accordingly, 12.3 g of dipalmitoylphosphatidylcholine and 5.1 g of palmitic acid were added to the solid residue, and the resulting mixture was suspended in distilled water and then lyophilized to obtain a yield of 54.4 g of surface active material. On analysis, this material was found to have a chemical composition as shown in Table VII.

EXAMPLE 2

The procedure of Example 1 was repeated except that the centrifugation of step (b) was carried out at 15,000 r.p.m. instead of 8,000 r.p.m. and the centrifugation of step (c) at 5,000 r.p.m. instead of 8,000 r.p.m. Thus, 44.2 g of solid residue was obtained in step (f).

This solid residue had a phospholipid content of 86.3%, a neutral fat content of 0.1%, and a free fatty acid content of 0.8%, all based on the total dry weight thereof, as well as a phosphatidylcholine content of 55.8% based on the total weight of phospholipid. Accordingly, 28.1 g of dipalmitoylphosphatidylcholine, 1.2 g of tripalmitoylglycerol, 1.3 g of trioleoylglycerol, 6.4 g of palmitic acid, and 4.0 g of stearic acid were added to the solid residue, and the resulting mixture was lyophilized to obtain a yield of 85.2 g of surface active material. On analysis, this material was found to have a chemical composition as shown in Table VII.

EXAMPLE 3

The procedure of Example 1 was repeated except that the centrifugation of step (b) was carried out at 18,000 r.p.m. instead of 8,000 r.p.m. and the centrifugation of step (c) at 12,000 r.p.m. instead of 8,000 r.p.m., the specific gravity of the crude sediment suspension prepared in step (c) was adjusted to 1.10 instead of 1.20, and the concentration of the aqueous sodium chloride solution used in step (c) was altered from 26.0% (w/v) to 13.0% (w/v). Thus, 24.0 g of solid residue was obtained in step (f). This solid residue had a phospholipid content of 92.8%, a neutral fat content of 0.2%, and a free fatty acid content of 1.5%, all based on the total dry weight thereof, as well as a phosphatidylcholine content of 57.9% based on the total weight of phospholipid. Accordingly, 11.0 g of dipalmitoyl phosphatidylcholine, 1.0 g of tripalmitoylglycerol, and 0.7 g of tristearoylglycerol were added to the solid residue, and the resulting mixture was suspended in distilled water and then lyophilized to obtain a yield of 36.7 g of surface active material. This material had a chemical composition as shown in Table VII.

EXAMPLE 4

The procedure of Example 1 was repeated except that, in step (e), the 11 liters of ethyl acetate and 7 liters of chloroform-methanol (with a volume ratio of 2:1) were replaced by 15 liters of propyl acetate and 10 liters of chloroform-ethanol (with a volume ratio of 2:1), respectively. Thus, 32.8 g of solid residue was obtained in step (f). This solid residue had a phospholipid content of 72.8%, a neutral fat content of 10.5%, and a fatty acid content of 0.2%, all based on the total dry weight thereof, as well as a phosphatidylcholine content of 48.1% based on the total weight of phospholipid. Accordingly, 5.9 g of phosphatidylcholine, 2.1 g of palmitic acid, and 0.5 g of oleic acid were added to the solid residue, and the resulting mixture was suspended in distilled water and then lyophilized to obtain a yield of 41.3 g of surface active material. This material had a chemical composition as shown in Table VII.

EXAMPLE 5

The procedure of Example 1 was repeated except that the centrifugation of step (b) was carried out at 20,000 r.p.m. instead of 8,000 r.p.m. and the 7 liters of chloroform-ethanol (with a volume ratio of 2:1) used in step (e) was replaced by 10 liters of ether-ethanol (with a volume ratio of 1:3). Thus, 28.3 g of solid residue was obtained in step (f). This solid residue had a phospholipid content of 85.5%, a neutral fat content of 0.1%, and a free fatty acid content of 0.6%, all based on the total weight thereof, as well as a phosphatidylcholine content of 54.2% based on the total weight of phospholipid. Accordingly, 8.9 g of phosphatidylcholine, 5.9 g of tristearoylglycerol, and 2.5 g of palmitic acid were added to the solid residue, and the resulting mixture was suspended in distilled water and then lyophilized to obtain a yield of 45.6 g of surface active material. This material had a chemical composition as shown in Table VII.

EXAMPLE 6

The procedure of Example 1 was repeated except that 35.5 kg of lungs excised from horses were used in place of the 32.0 kg of lungs excised from cattle. Thus, 34.5 g of solid residue was obtained in step (f). This solid residue had a phospholipid content of 80.1%, a neutral fat content of 0.2%, and a free fatty acid content of 0.9%, all based on the total dry weight thereof, as well as a phosphatidylcholine content of 53.8% based on the total weight of phospholipid. Accordingly, 21.0 g of dipalmitoylphosphatidylcholine, 6.0 g of tripalmitoylglycerol, 2.0 g of trioleoylglycerol, 1.0 g of palmitic acid, 0.3 g of stearic acid, and 0.5 g of oleic acid were added to the solid residue, and the resulting mixture was suspended in distilled water and then lyophilized to obtain a yield of 65.0 g of surface active material. This material had a chemical composition as shown in Table VII.

EXAMPLE 7

The procedure of Example 1 was repeated except that 28.5 kg of lungs excised from sheep were used in place of the 32.0 kg of lungs excised from cattle. Thus, 28.3 g of solid residue was obtained in step (f). This solid residue had a phospholipid content of 55.6%, a neutral fat content of 13.9%, and a free fatty acid content of 17.4%, all based on the total dry weight thereof, as well as a phosphatidylcholine content of 70.1% based on the total weight of phospholipid. Accordingly, 15.5 g of dipalmitoylphosphatidylcholine was added to the solid residue, and the resulting mixture was suspended in distilled water and then lyophilized to obtain a yield of 40.8 g of surface active material. On analysis, this material was found to have a chemical composition as shown in Table VII.

EXAMPLE 8

The procedure of Example 1 was repeated except that 30.0 kg of lungs excised from pigs were used in place of the 32.0 kg of lungs excised from cattle. Thus, 29.8 g of solid residue was obtained in step (f). This solid residue had a phospholipid content of 89.3%, a neutral fat content of 0.2%, and a free fatty acid content of 0.7%, all based on the total dry weight thereof, as well as a phosphatidylcholine content of 76.8% based on the total weight of phospholipid. Accordingly, 1.0 g of tripalmitoylglycerol, 0.5 g of tristearoylglycerol, 4.2 g of palmitic acid, and 1.3 g of oleic acid were added to the solid residue, and the resulting mixture was suspended in distilled water and then lyophilized to obtain a yield of 36.8 g of surface active material. This material had a chemical composition as shown in Table VII.

EXAMPLE 9

(a) The lungs (2.8 kg) excised from a 0-month-old calf were washed with water to remove any blood and other contaminants adhering thereto. Then, the lungs were cut into fist-sized lumps, freed of unnecessary blood vessels, windpipes, fat bodies and the like with the acid of scissors, and washed again with water. These lumps were finely minced with a meat grinder to obtain 2.5 kg of lung mince. This lung mince was added to 15.0 liters of physiological saline. The resulting mixture was stirred at 4° C. for 2 hours, placed in a filter bag, and filtered under a pressure of 120 kg/cm² to obtain an extract. Thereafter, 5.0 liters of physiological saline was poured over the filtration residue and diltered again under pressure to obtain an additional extract. The combined volume of the extract thus obtained was 19.5 liters.

(b) The above extract was centrifuged at 13,000 r.p.m. at 5° C. for 40 minutes to collect a crude sediment. This crude sediment was suspended in 2.0 liters of physiological saline and then centrifuged at 700 r.p.m. at 5° C. for 10 minutes to precipitate off any residual tissue fragments and the like.

(c) To the suspension obtained as the top layer was added sodium chloride in small portions so as to adjust its specific gravity to approximately 1.15. The adjusted suspension was centrifuged at 10,000 r.p.m. at 5° C. for 30 minutes to divide it into three layers, the top layer being an emulsified scum layer. This top layer was isolated and purified by re-suspending it in 1.0 liter of a 25.5% (w/v) aqueous sodium chloride solution and centrifuging the resulting suspension at 10,000 r.p.m. for 30 minutes.

(d) The purified top layer was suspended in distilled water and the resulting suspension was dialyzed through a cellophane membrane against distilled water. Thereafter, the dialyzed suspension was lyophilized to obtain 19.5 g of crude dry product.

(e) This crude dry product was added to 1,200 ml of cold ethyl acetate at 5° C. The resulting mixture was stirred for 20 minutes and then filtered under reduced pressure to separate an insoluble material. After this insoluble material was dried, 650 ml of an organic solvent mixture, or chloroform-methanol (with a volume ratio of 2:1), was added thereto. The resulting mixture was stirred for 20 minutes and then filtered through filter paper to obtain 630 ml of purified filtrate. When a sterility test was made on a small sample of this purified filtrate, it was found to be sterile. Accordingly, all subsequent operations were carried out under sterile conditions.

(f) The above purified filtrate was concentrated under reduced pressure to obtain 1.6 g of solid residue. This solid residue had a phospholipid content of 83.6%, a neutral fat content of 6.4%, and a free fatty acid content of 5.7%, all based on the total dry weight thereof, as well as a phosphatidylcholine content of 75.8% based on the total weight of phospholipid. Accordingly, the solid residue required no further treatment and could be regarded as a final product. This product had a chemical composition as shown in Table VII.

EXAMPLE 10

The procedure of Example 9 was repeated except that the lungs (3.5 kg) excised from a 4-months-old calf were used in place of the lungs (2.8 kg) excised from a 0-month-old calf. Thus, 3.4 g of solid residue was obtained in step (f). This solid residue had a phospholipid content of 94.8%, a neutral fat content of 0.4%, and a free fatty acid content of 0.5%, all based on the total dry weight thereof, as well as a phosphatidylcholine content of 80.2% based on the total weight of phospholipid. Accordingly, 1.3 g of palmitic acid was added to the solid residue, and the resulting mixture was suspended in distilled water and then lyophilized to obtain a yield of 4.7 g of surface active material. This material had a chemical composition as shown in Table VII.

EXAMPLE 11

The procedure of Example 9 was repeated except that the lungs (2.0 kg) excised from a 3-months-old young pig were used in place of the lungs excised from a calf. Thus, 2.8 g of solid residue was obtained in step (f). This solid residue had a phospholipid content of 78.3%, a neutral fat content of 1.8%, and a free fatty acid content of 15.5%, all based on the total dry weight thereof, as well as a phosphatidylcholine content of 54.8% based on the total weight of phospholipid. Accordingly, 0.6 g of phosphatidylcholine was added to the solid residue, and the resulting mixture was suspended in distilled water and then lyophilized to obtain a yield of 3.4 g of surface active material. This material had a chemical composition as shown in Table VII.

TABLE VII

| Example No. | 1 | 2 | 3 | 4 | 5 | 6 | 7 | 8 | 9 | 10 | 11 |
|---|---|---|---|---|---|---|---|---|---|---|---|
| Composition of surface active material (%) | | | | | | | | | | | |
| Phospholipid | 76.0 | 77.8 | 90.7 | 72.1 | 72.6 | 74.8 | 76.6 | 72.3 | 83.6 | 68.6 | 82.1 |
| Neutral fat | 7.0 | 3.0 | 4.8 | 8.3 | 13.0 | 12.4 | 9.6 | 4.2 | 6.4 | 0.3 | 1.5 |
| Triacylglycerols | 6.5 | 2.5 | 4.3 | 7.2 | 10.0 | 9.8 | 7.6 | 3.0 | 5.5 | 0.2 | 1.0 |
| Diacylglycerols | 0.3 | 0.4 | 0.5 | 1.1 | 2.5 | 2.0 | 1.5 | 0.8 | 0.8 | 0.1 | 0.2 |
| Monoacylglycerols | 0.2 | 0.1 | 0.0 | 0.0 | 0.5 | 0.6 | 0.5 | 0.4 | 0.1 | 0.0 | 0.3 |
| Total cholesterol | 0.6 | 1.3 | 0.4 | 8.0 | 1.2 | 3.1 | 0.1 | 0.0 | 0.0 | 0.7 | 0.8 |
| Free cholesterol | 0.5 | 0.7 | 0.4 | 6.5 | 1.0 | 2.7 | 0.1 | 0.0 | 0.0 | 0.4 | 0.7 |
| Cholesterol esters | 0.1 | 0.6 | 0.0 | 1.5 | 0.2 | 0.4 | 0.0 | 0.0 | 0.0 | 0.3 | 0.1 |
| Free fatty acids | 9.7 | 12.6 | 1.0 | 6.5 | 5.9 | 2.8 | 12.0 | 15.5 | 5.7 | 27.7 | 12.8 |
| Carbohydrate | 0.5 | 0.4 | 0.5 | 0.3 | 1.3 | 1.0 | 0.1 | 2.0 | 1.0 | 0.2 | 0.6 |
| Protein | 1.3 | 0.0 | 1.0 | 1.1 | 3.5 | 2.1 | 0.2 | 0.7 | 0.9 | 0.5 | 0.3 |
| Water | 4.8 | 5.0 | 1.8 | 3.8 | 2.5 | 4.5 | 1.6 | 5.2 | 2.4 | 2.1 | 2.0 |
| Phospholipid constituents (%) | | | | | | | | | | | |
| Phosphatidylcholine | 65.4 | 74.5 | 71.8 | 58.4 | 66.5 | 73.8 | 85.0 | 76.8 | 75.8 | 80.2 | 64.5 |
| Phosphatidylglycerol | 8.5 | 1.3 | 5.3 | 7.7 | 12.0 | 2.2 | 1.1 | 6.9 | 3.0 | 0.1 | 7.3 |
| Phosphatidylethanolamine | 8.7 | 9.5 | 12.6 | 6.4 | 8.0 | 5.7 | 7.1 | 4.8 | 3.5 | 7.1 | 11.5 |
| Sphingomyelin | 7.8 | 3.2 | 5.2 | 10.1 | 4.0 | 5.1 | 4.0 | 7.8 | 11.1 | 5.9 | 12.1 |
| Phosphatidylinositol | 1.2 | 3.8 | 1.9 | 6.6 | 2.1 | 3.9 | 1.5 | 2.0 | 4.5 | 2.7 | 2.8 |

TABLE VII-continued

| Example No. | 1 | 2 | 3 | 4 | 5 | 6 | 7 | 8 | 9 | 10 | 11 |
|---|---|---|---|---|---|---|---|---|---|---|---|
| Phosphatidylserine | 6.4 | 4.2 | 2.0 | 5.5 | 5.7 | 1.4 | 1.0 | 1.1 | 1.5 | 2.1 | 1.2 |
| Lysophosphatidylcholine | 0.5 | 1.1 | 0.3 | 1.8 | 1.7 | 2.9 | 0.1 | 0.1 | 0.2 | 0.5 | 0.4 |
| Others | 1.5 | 2.4 | 0.9 | 3.5 | 0.0 | 5.0 | 0.2 | 0.5 | 0.4 | 1.4 | 0.2 |
| Content of phosphatidylcholine having two saturated fatty acid residues (%) | 75.6 | 70.9 | 77.6 | 69.4 | 61.3 | 73.2 | 83.1 | 73.8 | 82.6 | 87.5 | 78.9 |

What is claimed is:

1. A surface active material comprising (1) phospholipid, neutral fat, total cholesterol, free fatty acids, carbohydrate, protein and water, all of which are obtained from the lung tissue of a mammal, and (2) optionally at least one additional component selected from the group consisting of a phosphatidylcholine, a neutral fat and a free fatty acid, characterized in that the overall phospholipid content is 68.6–90.7%, the overall neutral fat content is 0.3–13.0%, the total cholesterol content is 0.0–8.0%, the overall free fatty acid content is 1.0–27.7%, the carbohydrate content is 0.1–2.0%, the protein content is 0.0–3.5%, and the water content is 2.1–5.2%, all based on the dry weight of the material, the surface tension of the material as measured at 15°–25° C. by Wilhelmy's method in which the material is added dropwise to the surface of physiological saline in an amount of 0.3–0.8 $\mu$g per square centimeter of the surface area thereof being 30.1–47.5 dynes/cm when the surface area is 54.0 cm$^2$.

2. A surface active material as claimed in claim 1 wherein the overall phospholipid content is estimated by multiplying its phosphorus content by 25; the overall neutral fat content is estimated by expressing its constituents in terms of mono-, di- and trioleoylglycerols and then calculating the sum total thereof; the total cholesterol content was estimated by expressing its constituents in terms of free cholesterol and cholesterol palmitate and then calculating the sum total thereof; and the overall free fatty acid content, the carbohydrate content and the protein content are expressed in terms of palmitic acid, glucose and bovine serum albumin, respectively.

3. A surface active material as claimed in claim 1 wherein the phospholipid consists essentially of, on a weight basis, 58.4–85.0% of phosphatidylcholine, 0.1–12.0% of phosphatidylglycerol, 3.5–12.6% of phosphatidylethanolamine, and 3.2–12.1% of sphingomyelin.

4. A surface active material as claimed in claim 3 wherein the content of phosphatidylcholine having two saturated fatty acid residues based on the total weight of phosphatidylcholine is 61.3–87.5%.

5. A surface active material as claimed in claim 1, 2, 3 or 4 wherein the phosphatidylcholine optionally used as an additional component is dipalmitoylphosphatidylcholine.

6. A surface active material as claimed in claim 1, 2, 3 or 4 wherein the neutral fat optionally used as an additional component is a member selected from the group consisting of tripalmitoylglycerol, tristearoylglycerol, trioleoylglycerol and mixtures thereof.

7. A surface active material as claimed in claim 1, 2, 3 or 4 wherein the fatty acid optionally used as an additional component is a member selected from the group consisting of palmitic acid, stearic acid, oleic acid and mixtures thereof.

8. A surface active material as claimed in claim 1, 2, 3 or 4 wherein the mammal is selected from the group consisting of cattle, horses, sheep and pigs.

9. A pharmaceutical composition useable for the treatment of respiratory distress syndrome comprising an effective amount of a surface active material as set forth in claim 1 and a pharmaceutically acceptable carrier thereof.

10. A pharmaceutical composition as claimed in claim 9 wherein the effective amount for adult patients is between 500 and 3,000 mg per treatment.

11. A pharmaceutical composition as claimed in claim 9 wherein the effective amount for premature infants is between 50 and 400 mg per treatment.

12. A pharmaceutical composition as claimed in claim 9, 10 or 11 wherein the carrier is selected from the group consisting of water and an electrolyte solution.

13. A pharmaceutical composition as claimed in claim 12 wherein the electrolyte solution is physiological saline.

14. A pharmaceutical composition as claimed in claim 9, 10 or 11 wherein the effective amount is administered directly into the airway of patients with respiratory distress syndrome.

15. A pharmaceutical composition as claimed in claim 14 wherein the effective amount is administered in the form of a suspension.

16. A method of producing a surface active material comprising (1) phospholipid, neutral fat, total cholesterol, free fatty acids, carbohydrate, protein and water, all of which are obtained from the lung tissue of a mammal, and (2) optionally at least one additional component selected from the group consisting of a phosphatidylcholine, a neutral fat and a free fatty acid, characterized in that the overall phospholipid content is 68.6–90.7%, the overall neutral fat content is 0.3–13.0%, the total cholesterol content is 0.0–8.0%, the overall free fatty acid content is 1.0–27.7%, the carbohydrate content is 0.1–2.0%, the protein content is 0.0–3.5%, and the water content is 2.1–5.2%, all based on the dry weight of the material, the surface tension of the material as measured at 15°–25° C. by Wilhelmy's method in which the material is added dropwise to the surface of physiological saline in an amount of 0.3–0.8 $\mu$g per square centimeter of the surface area thereof being 30.1–47.5 dynes/cm when the surface area is 54.0 cm$^2$, the method comprising the steps of:

(a) bringing the minced lung tissue of a mammal into contact with an electrolyte solution to obtain an extract;

(b) centrifuging the extract to collect a crude sediment;

(c) adjusting the specific gravity of an aqueous suspension of the crude sediment by the addition of sodium chloride and centrifuging the adjusted suspension to isolate a top layer comprising an emulsified scum layer;

(d) dialyzing an aqueous suspension of the top layer and lyophilizing the dialyzed suspension to obtain a crude dry product;

(e) bringing the crude dry product into contact with an acetic acid ester to collect a material insoluble in the acetic acid ester and then bringing the insoluble material into contact with an organic solvent mixture to obtain a purified filtrate; and (f) concentrating the purified filtrate to obtain a solid residue, optionally adding to the solid residue at least one additional component selected from the group consisting of a phosphatidylcholine, a neutral fat and a free fatty acid, so as to provide an overall phospholipid content of 68.6–90.7%, an overall neutral fat content of 0.3–13.0%, and an overall free fatty acid content of 1.0–27.7%, all based on the dry weight of the final product, at well as an overall phosphatidylcholine content of 58.4–85.0% based on the total weight of phospholipid, and then lyophilizing the resulting mixture.

17. A method as claimed in claim 16 wherein the lung tissue minced with a meat grinder is used in step (a).

18. A method as claimed in claim 16 wherein the electrolyte solution used in step (a) is physiological saline.

19. A method as claimed in claim 16 wherein, in step (c), the specific gravity of the aqueous suspension of the crude sediment is adjusted to 1.10–1.20.

20. A method as claimed in claim 16 wherein, in step (d), the aqueous suspension of the top layer is dialyzed through a cellophane membrane.

21. A method as claimed in claim 16 wherein, in step (e), 1 part of the crude dry material is suspended in 20–200 parts of the acetic acid ester at a temperature of −10° to 10° C.

22. A method as claimed in claim 21 wherein the acetic acid ester is selected from the group consisting of methyl acetate, ethyl acetate, propyl acetate and butyl acetate.

23. A method as claimed in claim 16 wherein, in step (e), 1 part of the material insoluble in the acetic acid ester is suspended in 20–200 parts of the mixed organic solvent.

24. A method as claimed in claim 23 wherein the organic solvent mixture is selected from the group consisting of chloroform-methanol with a volume ratio of 2:1, chloroform-ethanol with a volume ratio of 2:1, chloroform-isopropanol with a volume ratio of 2:1, and ether-ethanol with a volume ratio of 1:3.

25. A method as claimed in claim 16 wherein, in step (f), the phosphatidylcholine optionally added to the solid residue is dipalmitoylphosphatidylcholine.

26. A method as claimed in claim 16 wherein, in step (f), the neutral fat optionally added to the solid residue is a member selected from the group consisting of tripalmitoylglycerol, tristearoylglycerol, trioleoylglycerol and mixtures thereof.

27. A method as claimed in claim 16 wherein, in step (f), the free fatty acid optionally added to the solid residue is a member selected from the group consisting of palmitic acid, stearic acid, oleic acid and mixtures thereof.

28. A method as claimed in claim 16 wherein the centrifugation of step (b) is carried out at 8,000–20,000 r.p.m. and the centrifugation of step (c) is carried out at 5,000–13,000 r.p.m.

29. A method as claimed in claim 16 wherein the mammal used in step (a) is selected from the group consisting of cattle, horses, sheep and pigs.

30. A method as claimed in claim 29 wherein 0- to 4-months-old calves are used.

31. A method as claimed in claim 29 wherein 3-months-old young pigs are used.

* * * * *

UNITED STATES PATENT AND TRADEMARK OFFICE

CERTIFICATE EXTENDING PATENT TERM
UNDER 35 U.S.C. § 156

PATENT NO.:     4,397,839

DATED:          August 9, 1983

INVENTOR:       Yuji Tanaka

PATENT OWNER:   Tokyo Tanabe Company, Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,262 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks